United States Patent [19]

Taheri

[11] Patent Number: 4,872,874
[45] Date of Patent: Oct. 10, 1989

[54] METHOD AND APPARATUS FOR TRANSARTERIAL AORTIC GRAFT INSERTION AND IMPLANTATION

[76] Inventor: Syde A. Taheri, 268 Dan Troy, Williamsville, N.Y. 14221

[21] Appl. No.: 56,131

[22] Filed: May 29, 1987

[51] Int. Cl.⁴ .......................... A61F 2/06; A61B 17/04
[52] U.S. Cl. ..................................... 623/1; 128/334 R
[58] Field of Search ................................ 623/1, 12, 66; 128/334 R, 334 C; 604/96, 104, 49, 343

[56] References Cited

U.S. PATENT DOCUMENTS

| | | | |
|---|---|---|---|
| 4,140,126 | 2/1979 | Choudhury | 623/1 X |
| 4,577,631 | 3/1986 | Kreamee | 128/334 R |
| 4,733,665 | 3/1988 | Palmaz | 623/1 X |
| 4,739,762 | 4/1988 | Palmaz | 623/1 X |
| 4,787,899 | 11/1988 | Lazarus | 623/1 |

*Primary Examiner*—Alan W. Cannon
*Attorney, Agent, or Firm*—Sommer & Sommer

[57] ABSTRACT

A method for implanting a tubular graft within a preselected blood vessel utilizes apparatus embodiments for inserting the graft endwise and axially through the blood vessel into place therein and for operatively securing the graft to the inside wall of the blood vessel with surgical staple-like clips. For inserting the graft through the blood vessel, an apparatus embodiment includes a lengthy conduit for insertion through the blood vessel and having a distal end adapted to selectively expand and contract for cooperating with a preformed hole in the sidewall of the graft for binding the graft to or releasing the graft from the distal end. For securing the graft to the wall of the blood vessel, an apparatus embodiment includes an inflatable body adapted to retain the staple-like clips in a circular formation so that the pointed legs of the clips are directed generally radially outwardly of the circular formation and a mechanism for abruptly inflating the inflatable body to thereby drive the clips radially outwardly and through the wall of the tubular graft. A magnet can be used to retain the clips in condition against the inflatable body prior to being driven outwardly as aforesaid. The method of the invention includes the steps involved in implanting the tubular graft in the preselected blood vessel.

4 Claims, 3 Drawing Sheets

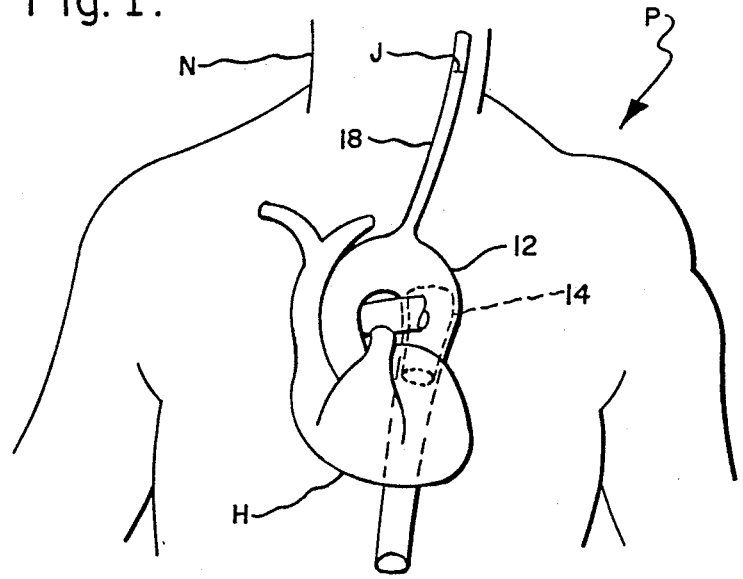
Fig. 1.
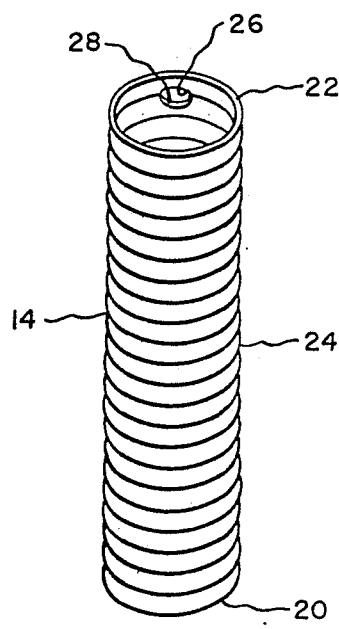
Fig. 2.
Fig. 3.
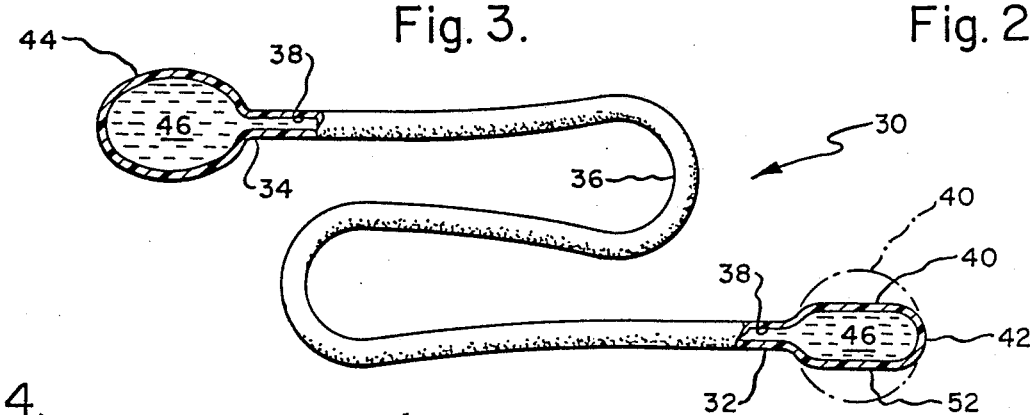
Fig. 4.
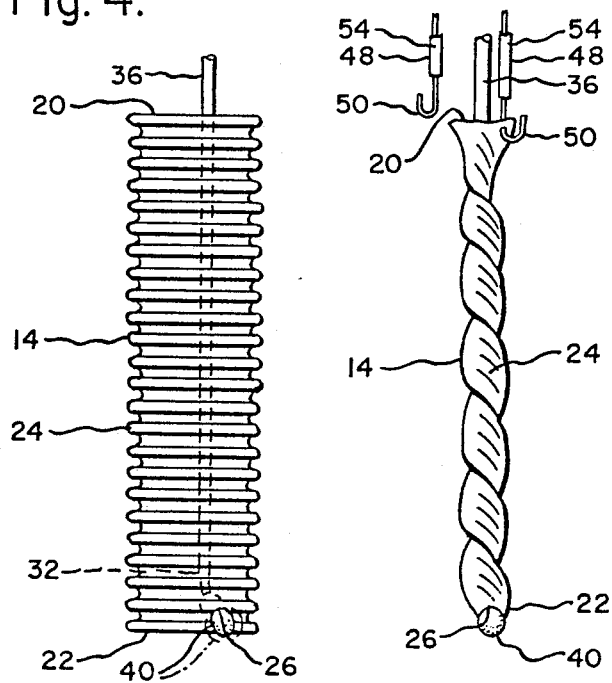
Fig. 5.
Fig. 6.
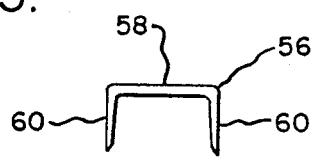

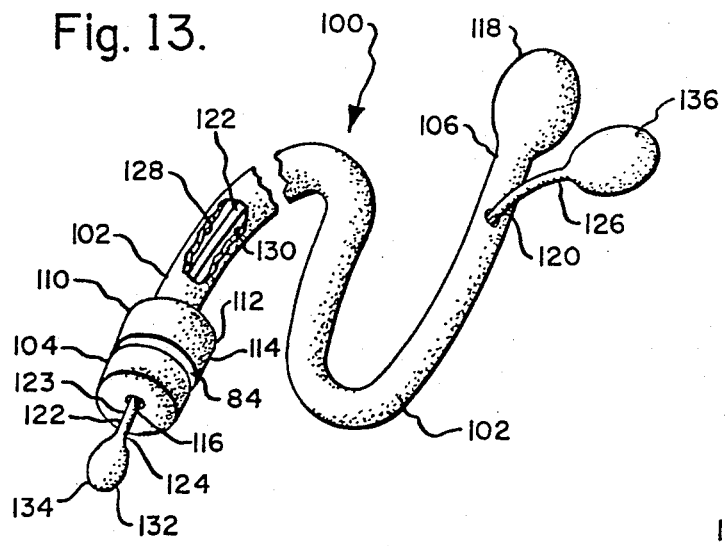
Fig. 13.
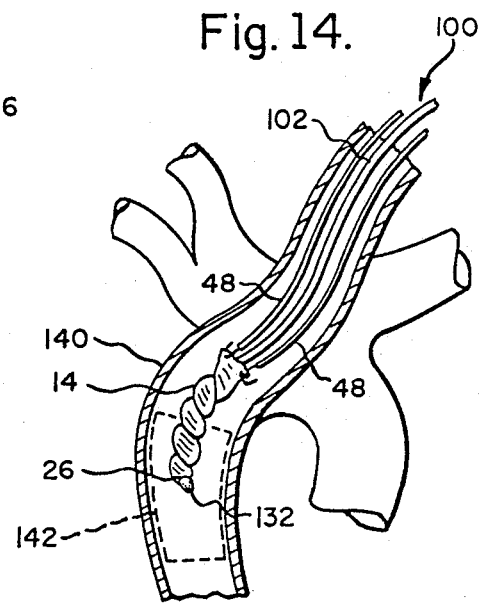
Fig. 14.
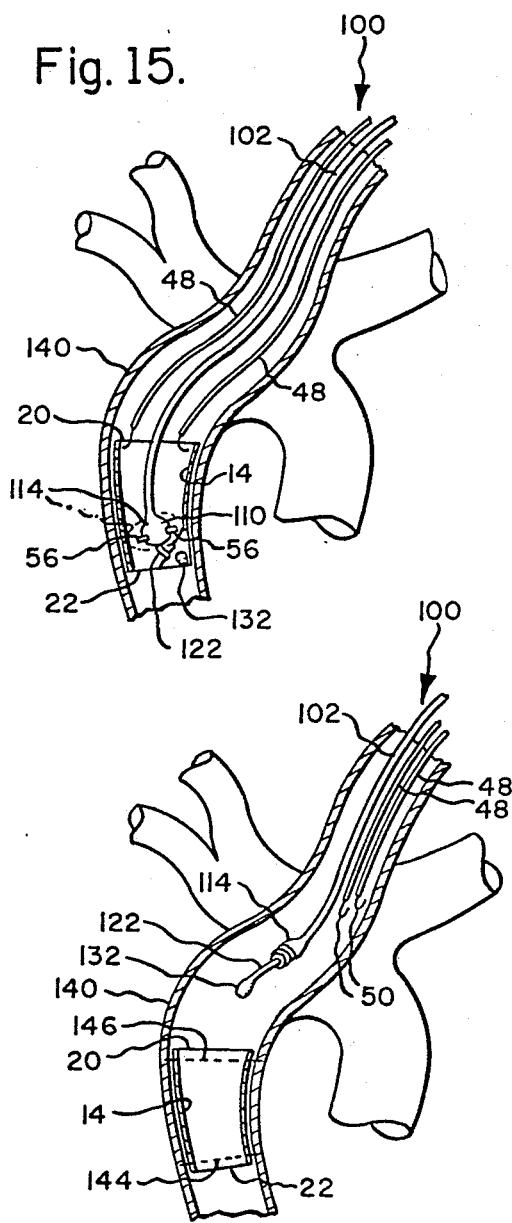
Fig. 15.
Fig. 17.
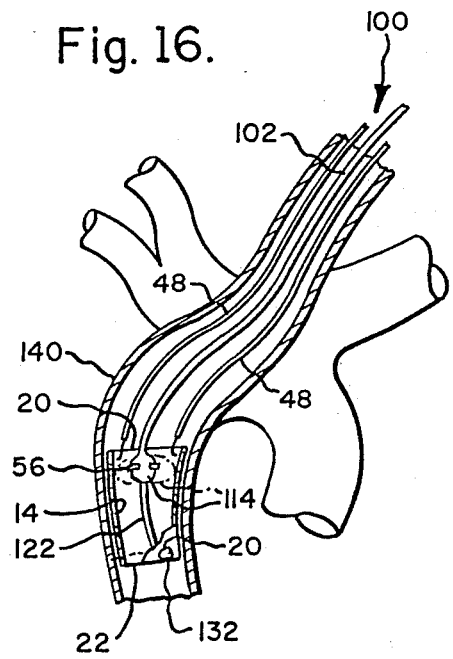
Fig. 16.

METHOD AND APPARATUS FOR TRANSARTERIAL AORTIC GRAFT INSERTION AND IMPLANTATION

BACKGROUND OF THE INVENTION

This invention relates generally to surgical methods and apparatus and relates more particularly to apparatus and methods for implanting a graft within a preselected blood vessel such as the aorta.

It is known that a tubular graft can be implanted within the aorta of a patient by surgically insizing or sectioning the aorta through the patient's abdomen, inserting the graft through the formed incision and operatively attaching the graft to the wall of the aorta by means of staple-like clips. Such implanting operations, however, are not without risks, and the mortality rate during such operations is presently estimated as ranging between about four to seven percent. Deaths occurring during such implanting operations are believed to be due, at least in part, to the insizing or sectioning of the patient's aorta and abdomen for the implanting of the graft.

It is an object of the present invention to provide a new and improved apparatus and method for implanting a tubular graft within a preselected blood vessel, such as the aorta.

Another object of the present invention is to provide such a method which circumvents any need to section the abdomen or aorta of the patient and is thereby believed to effectively reduce the mortality rate during such implanting operations.

Still another object of the present invention is to provide such apparatus which is relatively uncomplicated in construction and effective in operation.

SUMMARY OF THE INVENTION

This invention resides in a method and apparatus for implanting a tubular graft within a preselected blood vessel such as the aorta of the heart. The tubular graft has a sidewall extending between its opposite ends and for purposes of implanting the graft with apparatus of the invention and in accordance with method of the invention, the sidewall defines a preformed hole adjacent one of the graft ends.

A device embodiment of the apparatus of the invention is utilized for holding the graft while the graft is being inserted endwise through a blood vessel into a desired position therein. The device includes lengthy means defining a distal end and a proximal end and is of such size to be inserted distal-end first through the blood vessel with the graft positioned about the distal end. A distensible bulb is associated with the distal end of the lengthy means and is adapted to be selectively contracted and expanded between a contracted condition, at which the distensible bulb is loosely receivable between the preformed opening in the sidewall of the graft, and an expanded condition at which the bulb, when operatively positioned within the preformed opening, cooperates therewith to bind the graft to the distal end. The device further includes means associated with the distensible bulb for selectively expanding and contracting the bulb so that when the distal end is inserted endwise through the end of the graft opposite the preformed hole and the bulb is positioned and expanded within the preformed opening so as to bind the graft to the distal end, the distal end securely retains the graft for operative insertion through a blood vessel.

An instrument apparatus of the invention is utilized for securing the tubular graft to the wall of a blood vessel utilizing staple-like clips. Each such clip is generally U-shaped in form and has a base portion and two parallel and pointed legs extending from the base portion. The instrument includes elongated means defining a distal end and a proximal end and adapted to be inserted distal-end first into a tubular graft when the graft is operatively positioned within the blood vessel. Retaining means are associated with the distal end of the elongated means for holding the clips in substantially a circular formation therearound so that the pointed legs of the clips are directed generally radially outwardly of the circular formation. The instrument further includes attachment means associated with the retaining means for driving the clips radially outwardly of the circular formation so that when the graft is operatively positioned within the blood vessel and the distal end of the elongate means is operatively positioned within the graft so that the clips held by the retaining means are arranged in a radial plane of the graft and the clips are driven radially outwardly as aforesaid, the pointed legs of the clips penetrate the wall of the graft and the wall of the vessel to thereby secure the graft between the wall of the blood vessel and the base portions of the clips.

The method of the invention includes the steps involved in implanting the tubular graft within the blood vessel with the device and instrument apparatus of this invention. Such steps include the opening of the preselected blood vessel to gain access therein at a location remote of the location at which the graft is ultimately desired to be implanted and inserting the tubular graft through the formed opening and endwise and axially through the preselected blood vessel until the graft is located in the ultimately-desired location therein. The staple-like clips are then driven through the wall of the graft and into the wall of the preselected blood vessel in a manner operatively securing the tubular graft within the preselected blood vessel.

BRIEF DESCRIPTION OF THE DRAWING FIGURES

FIG. 1 is a somewhat schematic view of a portion of the human body illustrating a blood vessel within which a tubular graft is desired to be positioned in accordance with the method of this invention.

FIG. 2 is a perspective view of a graft of the type to be positioned within the FIG. 1 blood vessel.

FIG. 3 is a perspective view, shown partially cut away, of a device embodiment in accordance with the apparatus of the present invention for inserting the FIG. 2 graft within the blood vessel.

FIG. 4 is a side view of the FIG. 2 graft and a fragment of the FIG. 3 device illustrating the operative securement between an end of the FIG. 3 device and FIG. 2 graft.

FIG. 5 is view similar to that of FIG. 4 of a FIG. 4 arrangement wherein the graft is positioned in a twisted condition about the end of the FIG. 3 device.

FIG. 6 is a plan view of a clip with which the FIG. 2 graft is fastened within the FIG. 1 blood vessel.

FIG. 13 is a fragmentary perspective view, shown partially cut-away, of an alternative apparatus in accordance with the present invention.

FIGS. 14–17 are somewhat schematic views of a blood vessel and the sequential steps involved in inserting and implanting the graft of FIG. 2 within the blood vessel by means of the FIG. 13 embodiment.

DETAILED DESCRIPTION OF THE ILLUSTRATED EMBODIMENTS

Figure 7:
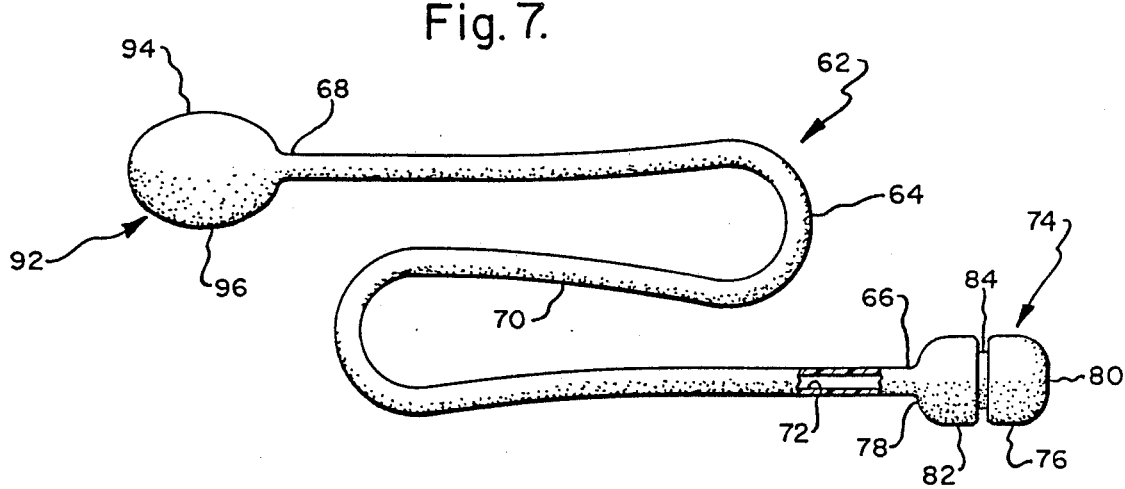
FIG. 7 is a perspective view, shown partially cut away, of an instrument embodiment in accordance with the apparatus of the present invention.

Turning now to the drawings in greater detail and considering first FIG. 1, there is shown a patient P, illustrated somewhat schematically, having a blood vessel 12 within which a tubular graft 14 (FIG. 2) is desired to be secured. The patient P includes a heart H and the blood vessel 12 within which the graft is to be positioned is the abdominal aorta which, as illustrated in FIG. 1, is joined to so as to extend from the upper side of the heart H. The patient P further includes an additional blood vessel, or carotid vessel 18, joined to the aorta 12 so as to be in generally direct flow communication therewith and so as to extend upwardly therefrom through the neck region N of the patient P.

The location within the aorta 12 at which the graft 14 is desired to be positioned is illustrated in phantom in FIG. 1. As will be described in greater detail hereinafter in connection with the apparatus of the invention, the graft 14 is inserted axially through the blood vessel 18 and into the aorta 12 and operatively secured to the wall of the aorta 12 by means of the apparatus of the present invention. For purposes of inserting the graft 14 into the blood vessel 18 and through the aorta 12, the blood vessel 18 is opened in the neck region N at about the location indicated J in FIG. 1.

With reference to FIG. 2, the tubular graft 14 of the type to be operatively positioned within the aorta 12 is elongated in shape so as to define two opposite ends 20,22. A sleeve-like sidewall 24 extends between the ends 20,22 and as shown in FIG. 2, is relatively thin and accordian-like to facilitate the bending of the graft 14 along the length thereof. The material out of which the graft is constructed is a relatively soft fabric but can be of a type commonly used in surgical graft applications.

For purposes of inserting the graft 14 axially through the blood vessesl 18 and 12 in a manner hereinafter described, the sidewall 24 of the graft 14 defines a relatively small preformed hole 26 adjacent the graft end 22. The hole 26 is cut or formed in the sidewall 24 by means of a knife (not shown) or similar instrument and, for a reason which will be apparent hereinafter is bounded by an edge 28.

With reference to FIG. 3, there is illustrated a device embodiment, generally indicated 30, in accordance with the apparatus of the present invention utilized for inserting the graft 14 through the blood vessels 18 and 12. The device 30 is lengthy and elongated in shape and defines a distal end portion 32 and a proximal end portion 34. Extending between the ends 32,34 is a flexible conduit 36 comprised of catheter tube material providing a fluid passageway 38 along the length thereof.

The device 30 further includes a generally rounded, distensible bulb 40 associated with the distal end 32 and adapted to be selectively expanded and contracted between a contracted condition as shown in solid lines in FIG. 3 and an expanded condition illustrated in phantom in FIG. 3. When in the contracted condition, the bulb 40 is loosely receivable by the preformed opening 26 (FIG. 2) in the graft 14 and when in its expanded condition cooperates with the preformed opening 26 to bind the graft 14 to the distal end 32 and prevent relative rotation between the graft end 22 and the distal end 32.

With reference still to FIG. 3, the bulb 40 includes a hollow inflatable body 46 comprised, for example, of synthetic rubber, and is provided with a degree of flexibility and stretchability is that the pressurizing and depressurizing of the hollow interior of the body 42 effects an expansion and contraction in size of the circumference of the body 42 taken about a radial plane of the body 42. The bulb 40 is of such size and shape that the distal end 32 of the device 30 can be directed distal-end-first and axially through a preselected blood vessel, such as blood vessel 12 or 18, with the graft 14 operatively positioned thereabout. Hence, the diameter of each of the bulb 30 and conduit 36 of the device are relatively small. Furthermore, the bulb 40 possesses a generally cylindrical mid-portion 52 between its ends.

For purposes of selectively expanding and contracting the bulb 40, the device 30 includes a hollow flexible protuberant 44 associated with the proximal end 34 of the device 30. The interior of the protuberant 44 is in flow communication with the interior of the bulb body 42 through the conduit passageway 38, and the interior of each of the protuberant 44 and bulb body 42 and passageway 38 are filled with a fluid 46 so that a squeezing or relaxing of the protuberant 44 moves the bulb body 42 between inflated and deflated conditions. Preferably, the fluid 46 is a relatively incompressible fluid, such as water, so that a squeezing of the protuberant 44 inflates the bulb body 42 a corresponding amount and a subsequent relaxing of the protuberant 44 deflates the bulb body 42 a corresponding amount. The protuberant 44 is of such size and shape to be squeezed or otherwise manipulated by hand.

To secure the graft 14 to the device 30 for operative insertion through the blood vessels 18 and 12 and with reference to FIG. 4, the device 30 is inserted distal-end-first through the graft end 20 and the bulb 40, when in its contracted condition, is manipulated into the preformed opening 26 so that the edge 28 of the opening 26 generally encircles the middle of the bulb 40. At that point, the protuberant 44 is squeezed to expand the bulb 40 so that its outer surface presses against the opening edge 28 in a radially outwardly direction so that the opening edge 28 is tightly held about the circumference of the bulb 40. In such a condition in which the bulb 40 tightly and snuggly received by the opening edge 28, the graft 14 is bound to the device 30 to releasably secure the graft end 22 to the bulb 40.

Once secured to the bulb 40 in the manner illustrated in FIG. 4, the graft end 20 is rotated relative to the distal end 32 to place the graft 14 in a twisted condition about the distal end 32 as illustrated in FIG. 5. During such a rotating operation, the graft end 22 is prevented from rotating relative to the distal end 32 by the aforedescribed securement between the bulb 40 and graft end 22. In the FIG. 5 twisted condition, the overall diameter of the assembly comprised of the graft 114 and distal end 30 is substantially reduced from the diameter of the secured assembly as illustrated in FIG. 4 so that the graft 14 can be more easily inserted through a blood vessel.

When inserting the graft 14 through the preselected blood vessels 18 and 12, the location of the graft 14 is traced by conventional flouroscopic techniques. Therefore, the distal end 32, with graft 14, is fed through a blood vessel, such as under a flouroscope, to the desired location in the blood vessel. Once the graft 14 is positioned in the desired location, the device 30 is rotated in a manner untwisting the graft 14 from the distal end 32. To hold the graft end 20 in position and to prevent the graft end 20 from rotating with the graft end 22 as the distal end 32 is rotated, a pair of sheathed guide wires or stylets 48 are secured to the graft end 20. More particularly, each stylet 48 includes a wire 50 having a hook at the end thereof for hooking and thereby securing the stylet 48 to the graft end 20 and an outer sheath 54 slidably positioned about the wire 50.

The stylets 48 are operatively secured to the graft end 20 at locations thereon which are generally diametrically opposed to one another and in the manner in which the stylet 48 shown positioned to the right of the conduit 36 is shown attached to the graft end 20. When secured as aforesaid, the stylets 48 are inserted through the blood vessels 18 and 12 with the distal end 40 of the device 30. Once the graft 14 has been positioned in the blood vessel or aorta 12 in the desired location therealong, the stylets 48 are held stationary with respect to the aorta 12 and the distal end 30 rotated relative to the aorta 12 in a direction untwisting the graft 14 therefrom. Once the graft 14 is completely untwisted and thereby resumes its FIG. 4 untwisted condition, the bulb 40 is contracted and withdrawn from the graft opening 26, the interior of the graft 14 and the blood vessels 12 and 18. At this point, the stylets 48 remain operatively secured to the graft end 20 to temporarily anchor the graft within the aorta until the graft 14 is permanently secured therein.

With reference to FIG. 6, there is shown a surgical staple-like clip 56 of the type used to permanently secure the graft 14 to the wall of the aorta 12. The clip 56 is relatively small, is constructed of metal and is in the shape of a U including a base portion 58 and two parallel and pointed legs 60 joined to so as to extend from the base portion 58. When used to secure the graft 14 to the wall of the aorta 12 in a manner hereinafter described, the legs 60 of the clip 56 penetrate in sequence the sidewall 24 of the graft 14 and the inner wall of the aorta 12 to thereby secure the sidewall 24 between the base portion 58 and the aorta wall.

Figure 8:
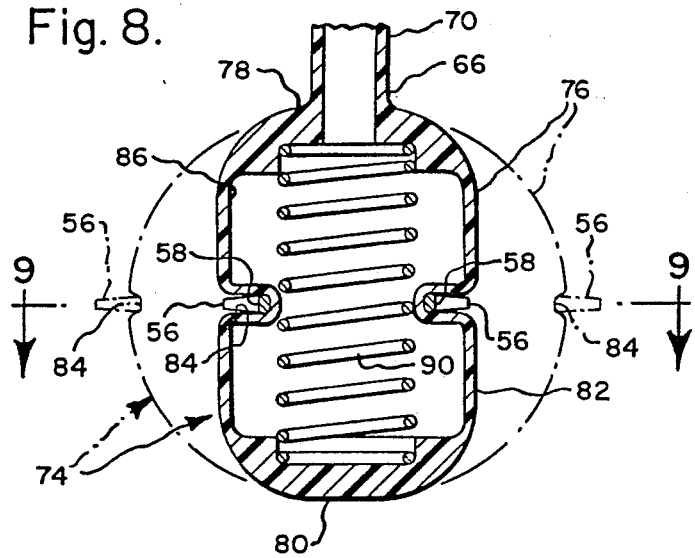
FIG. 8 is a longitudinal sectional view of the distal end of the FIG. 7 instrument within which a plurality of clips of the type illustrated in FIG. 6 are operatively positioned.
Figure 9:
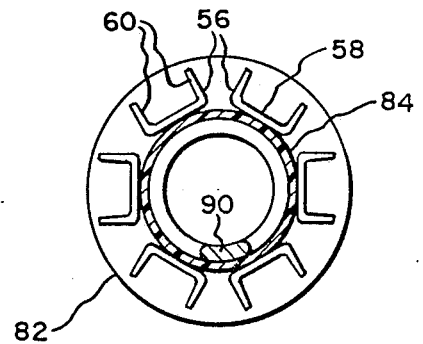
FIG. 9 is a cross-sectional view taken about on lines 9—9 of FIG. 8.

In accordance with the present invention and with reference to FIGS. 7-9, there is illustrated an instrument 62 in accordance with the apparatus of the present invention utilized for securing the graft 14 to the aorta 14 by means of the aforedescribed clips 56. The instrument 62 includes elongated means 64 defining a distal end 66 and a proximal end 68. Between the distal and proximal ends 66 and 68 is a flexible tube 70 within which is defined a passageway 72. The tube 70 is comprised of catheter tube material adapted to be received by the passageways provided by the blood vessels 18 and 12.

Associated with the distal end of the elongated means 64 are retaining means, generally indicated 74, for operatively holding a plurality of clips 56 in substantially a circular formation. To this end, the retaining means 74 includes an inflatable body 76 comprised, for example, of a soft plastic or synthetic rubber. The inflatable body 76 defines two opposite ends 78 and 80 and a substantially cylindrical surface 82 extending between the ends 78 and 80. The inflatable body 76 further includes means defining an annular recess or groove 84 positioned substantially midway along the length of the body 76. The groove 84 is adapted to retainably receive a plurality of clips 56,56 positioned therein in the manner illustrated in FIG. 9 so that the base portions 58 thereof effectively rest within the bottom of the groove 84 and the pointed legs 60,60 thereof are directed generally radially outwardly.

The inflatable body 76 is adapted to be inflated and deflated between an inflated condition as illustrated in phantom in FIG. 8 and a deflated condition as illustrated in solid lines in FIG. 8. To this end, the inflatable body 76 defines a cavity therein extending between the body end 78,80 and which is in flow communication with the passageway 72 defined within the tube 70. When the cavity 86 is selectively pressurized and depressurized in a manner hereinafter set forth, the surface 82 of the body 76 moves between the inflated and deflated conditions.

The instrument 62 further includes means for magnetically holding the clips 56 within the annular groove 84 when the body 76 is in its deflated condition. In the instrument embodiment 62, the holding means 88 includes a magnet 90 assuming the shape of a spring 92 positioned within the cavity 86 of the body 76. As best illustrated in FIG. 8, the magnet 90 is oriented axially through the body cavity 86 and has two opposite ends which cooperate with circular recesses defined at the opposite ends of the cavity for securing the magnet 90 therein. Because the clips 56,56 are constructed of metal, the magnet 90 magnetically attracts the clips 56 radially inwardly of the circular formation formed thereby and thereby retains the clips within the annular groove 84. An additional advantage provided by the magnet relates to its spring-like form. In particular, the magnet 90 effectively maintains a minimum diameter of the inflatable body 76 and thereby prevents the walls of the cavity 86 from collapsing upon one another.

Figure 10:
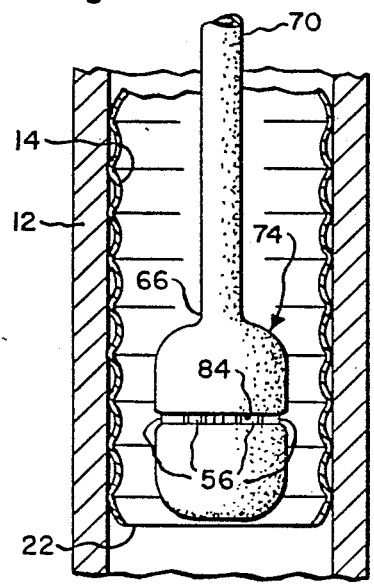
FIG. 10 is a longitudinal sectional view of the FIG. 1 blood vessel illustrating the FIG. 2 graft and distal end of the FIG. 7 device when operatively positioned therein and the distal end of the FIG. 7 device when in a collapsed condition.
Figure 11:
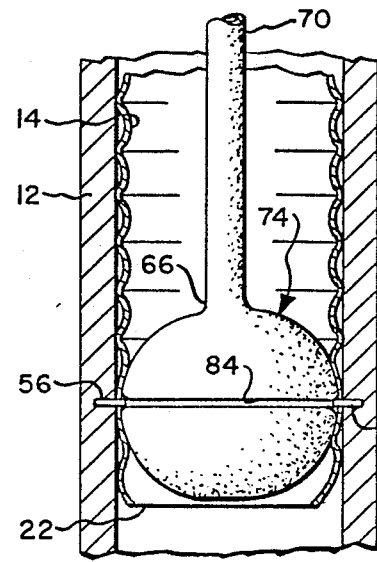
FIG. 11 is a view similar to that of FIG. 10 illustrating the distal end of the FIG. 7 device when in an expanded condition.

With reference to FIGS. 7, 10 and 11, the instrument 62 further includes attachment means 92 associated with the retaining means 74 for driving the clips radially outwardly of the circular formation between the deflated condition of the body 76 as illustrated in FIG. 10 and the inflated condition of the body 76 as illustrated in FIG. 11. To this end, there is associated with the proximal end 68 of the elongated means 64 inflating means 94 for abruptly inflating the inflatable body 76 to thereby drive the clips 56 radially outwardly of the body 76 and into the walls of the graft and blood vessel. The inflating means 94 is in the form of a hollow hand-manipulable protuberant 96 for selectively pressurizing and and depressurizing the deflatable body 76 when the protuberant 96 is abruptly squeezed or subsequently relaxed. The protuberant 96 is connected at the proximal end 68 so that its hollow interior is in flow communication with the cavity 86 of the inflatable body through the passageway 72 of the tube 70. The protuberant is constructed of a relatively flexible material, and the interiors of the protuberant 96, tube 70 and body 76 are filled with a suitable fluid, such as with an incompressible fluid, so that the squeezing or relaxing of the protuberant effects an inflation or deflation of the inflatable body 76 by a corresponding amount.

Figure 12:
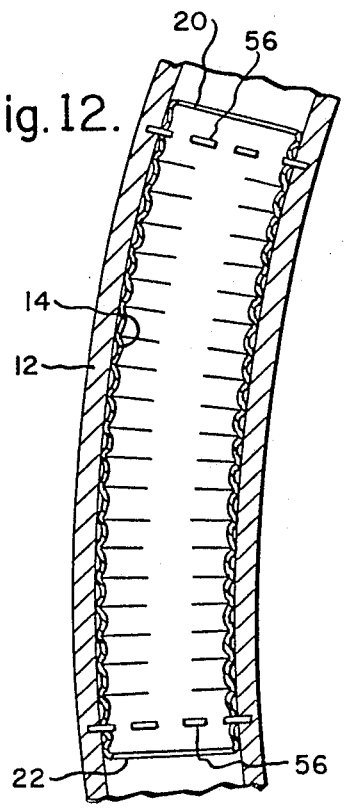
FIG. 12 is a longitudinal sectional view of the FIG. 1 blood vessel within which the FIG. 2 graft has been secured.

To operate the instrument 62 and thereby secure the clips 56 to the walls of the graft 14 and blood vessel 12, the distal end 96 of the instrument 62, within which a plurality of clips 56 are held, are inserted endwise through the blood vessels 18 and 12 until the inflatable body 76 is positioned adjacent the graft end 22. At that point, the inflatable body 76 is abruptly inflated by an abrupt squeezing of the attachment means 92 so that the clips 56 are driven radially outwardly in the manner depicted in FIG. 11 so that the pointed legs 60 of the clips pierce the sidewall of the graft 14 and an anterior wall of the blood vessel 12. Upon being driven through the wall of the graft and into the blood vessel wall, the inflatable body 76 is deflated thereby leaving the clips in the walls of the graft and blood vessel. It follows from the foregoing that the magnet 90 does not possess sufficient strength to pull or retract the clips 56 from the walls of the graft and blood vessel when the inflatble body 76 is deflated. Once the clips 56 have been operatively secured within the blood vessel 12 adjacent the graft end 22, the instrument 62 is removed from the blood vessels 18 and 12 reloaded with clips 56 and reinserted through the blood vessels 18 and 12 to secure the graft 14 to the blood vessel wall adjacent the graft end 20 in the manner that the graft end 22 was secured to the blood vessel. Briefly, the inflatable body 76 is positioned along the length of the blood vessel 12 so that the annular groove 84 is inside and adjacent the graft end 20. At that point, the inflatable body 76 is abruptly inflated to operatively drive the clips 56 through the sidewall of the graft 14 and into the wall of the blood vessel and deflated to thereby release the clips 56. The distal end 66 of the instrument 52 is thereafter withdrawn from the graft 14 and blood vessels 18 and 12, and the sytlets 48 unhooked from the graft end 20 and removed from the blood vessels 18,12. The tubular graft 14 is thereby secured, as shown in FIG. 12 at its opposite ends 20,22 so that the sidewall of the graft 14 is securely held between the inside wall of the blood vessel 12 and the base portions 58 of the clips 56.

With reference to FIG. 13, there is illustrated an alternative embodiment 100 of the apparatus of this invention which can be utilized for both inserting a tubular graft through a blood vessel and securing the graft to the sidewalls of the blood vessel. The apparatus embodiment 100 includes elongated means 102 having a distal end 104 and a proximal end 106 and which is of such size and shape to be received distal-end-first by a tubular graft 14 (FIG. 2). Retaining means 110 are associated with the distal end 104 of the elongated means 102 for holding clips 56 (FIG. 6) in substantially a circular formation so that the pointed legs of the clips 56 are directed generally radially outwardly of the circular formation. Attachment means 112 are associated with the retaining means 110 for driving the clips 56 radially outwardly of the circular formation.

The retaining means 110 is in the form of an inflatable body 114 through which is defined a hollow core 116. The attachment means 106 is in the form of a hollow hand-manipulable protuberant 118 connected at the proximal end 106 of the elongated means 102. The elongated means 102 is in the form of a flexible tube within which is defined a pair of parallel passageways 128,130. The passageway 128 is operatively joined between the hand-manipulable protuberant 118 and the inflatable body 114 and filled with an incompressible fluid so that a squeezing or subsequent relaxing of the protuberant 118 inflates and deflates the inflatable body 114 between a deflated condition such as the one illustrated in solid lines in FIG. 8 and an inflated condition such as the one illustrated in phantom in FIG. 8. For purposes of retaining the clips 56 (FIG. 6) in the aforementioned circular formation, the inflatable body 114 defines an annular groove 84 in the outer surface thereof and a magnetized spring (not shown) is mounted within the body 114. Hence, the clips 56 are positionable within the groove 84 so that the pointed legs thereof are directed radially outwardly and are retained therein by the magnetic attraction of the magnetized spring in condition for a subsequent driving outwardly of the clips 56 upon a squeezing of the protuberant 118.

The other passageway 130 of the elongated means 102 is connected at one end to the hollow core 116 of the body 114 and opens out of the side of the elongated means 102 at an opening 120 adjacent the proximal end 106 thereof for a reason which will be apparent hereinafter.

With reference still to FIG. 13, the apparatus 100 further includes lengthy means 122 in the form of a flexible hollow tube 123 having a distal end 124 and a proximal end 126 and associated with the elongated means 102 so that the distal end 124 corresponds with the distal end 104 of the elongated means 102. To this end, the lengthy means 122 is slidably received by the hollow core 116 of the inflatable body 114 and passageway 130 of the elongated means and extends out of the opening 120. Furthermore, the distal ends 124 and 104 are of such size to be inserted together through the tubular graft 14 (FIG. 2) for operative positioning therein.

A distensible bulb 132 is associated with the distal end of the lengthy means 122 and adapted to be selectively expanded and contracted between a contracted condition, at which the bulb 132 is loosely receivable by the preformed hole 26 (FIG. 2) of the graft 14, and an expanded condition at which the preformed hole 26, cooperates with the hole 26 to bind the graft 14 to the distal end 124. In the apparatus 100, the bulb 132 is in the form of a hollow inflatable body 134.

For purposes of selectively expanding and contracting the distensible bulb 132, the apparatus 100 includes a hollow flexible protuberant 136 associated with the proximal end 126 of the length means 122. More specifically, the interior of the protuberant 136 and the inflatable body 134 of bulb 132 communicate with one another through the hollow tube 123 and are filled with a relatively incompressible fluid so that a squeezing or subsequent relaxing of the protuberant 136 moves the bulb body 134 between the aforedescribed inflated and deflated conditions.

To utilize the apparatus 100 for inserting and implanting a graft 14 within a blood vessel 140 with reference to FIGS. 14-17, the distal ends 104 and 124 of the apparatus 100 are inserted through the graft end 20, and the bulb body 134 is operatively positioned and expanded within the preformed hole 26 of the graft 14 to thereby bind the graft 14 to the apparatus 100. The graft 14 is then twisted about the distal ends 104 and 124, and stylets 48 are operatively secured, or hooked, to the graft end 20. The graft 14 is then inserted in its twisted condition with the distal ends 104 and 124 of the apparatus 120 through a preformed opening in the blood vessel 140 at a location remote of the location 142, illustrated in phantom in FIG. 14, at which the graft 14 is desired to be positioned.

Once the graft 14 reaches the location 142, insertion ceases and the graft 14 is untwisted from the distal ends 104 and 124 so as to assume the condition illustrated in FIG. 15. The movement of the graft 14 through the blood vessel 140 can be traced by known flouroscopic techniques.

With the graft 14 held in a stationary position within the blood vessel 140 between the stylets 48 and the bulb body 132 as shown in FIG. 15, the inflatable body 114 of the retaining means 110 are operatively positioned along the length of the graft 114 at which the clips 56 are desired to be driven into the graft 14 and wall of the blood vessel 142. At that point, the protuberant 118 is abruptly squeezed to drive the clips 56 radially outwardly of the inflatable body 114 and thereby secure the graft 14 to the wall of the blood vessel 140. A subsequent relaxing of the protuberant 118 deflates the body 114 leaving the clips 56 affixed to the wall of the blood vessel 140.

For purposes of attaching each end of the graft 14 within the blood vessel 140, a first arrangement of clips 56 is secured at one end 22 of the graft 14 with the inflatable body 114 arranged adjacent the graft end 12 as shown in FIG. 15, and a second arrangement of clips 56 is secured at the other end 20 of the graft 14 with the body 114 arranged adjacent the graft end 20 as shown in FIG. 16. Because the lengthy means 122 is slidably received by the hollow core 116 and passageway 130, the inflatable body 114 can be shifted along the length of the lengthy means 122 to accomodate a repositioning of the body 114 therealong while the distensible bulb body 134 is maintained in an expanded or secured condition within the graft opening 26.

Furthermore, the sliding relationship between the elongated means 102 and lengthy means 122 permits the retaining means 110 to be withdrawn from the preformed opening in the blood vessel 140 for reloading of the retaining means 110 with clips 56 and reinserted within the blood vessel 140 while the graft 14 is held in a stationary condition thereby by means of the lengthy means 122 and stylets 98. It follows from the foregoing that the portion of the tube 123 of the lengthy means 122 extending out of the opening 120 defined in the side of the elongated means 102 is of sufficient length to accomodate a withdrawal of the retaining means 110 from the blood vessel 140 while the bulb body 134 of the lengthy means 122 remains secured to the graft 14.

Upon attachment of the first and second arrangement of clips, indicated 144 and 146, respectively, in FIG. 7, the apparatus 100, including both the elongated means 102 and lengthy means 122, are withdrawn from the blood vessel 140 through the preformed opening defined therein leaving the graft 14 operatively secured within the blood vessel 140. Furthermore, the stylets 48 are unhooked from the graft end 20 and withdrawn from the blood vessel 140. Upon completion of the operation as aforedescribed, the opening formed in the blood vessel 140 is closed off.

It will be understood that numerous substitutions and modifications can be had to the aforedescribed embodiments without departing from the spirit of the invention. For example, although the instrument embodiment 62 of FIGS. 7–11 has been described above as including a magnet 90, an instrument embodiment in accordance with the apparatus of the invention may not include such a magnet. Instead, the clips 56 may be retainably and releasably held by a suitable configuration, such as an annular groove, of the inflatable body of the instrument retaining means wherein a snug-fit relationship provided between the opposing walls of an annular groove and the clips 56 positioned therebetween. Furthermore, this invention contemplates the insertion and subsequent operative bending of the clips 56 through the graft sidewall and blood vessel wall by the instrument retaining means to enhance the securement of the graft to the wall of the blood vessel. Still further, although the inflatable and distensible bulbs discussed herein have been described as filled with an incompressible fluid, it will be understood that an inert gas, such as helium, can be used as a bulb-filling medium. Accordingly, the aforedescribed embodiments have been described for purposes of illustration and not as limitation.

I claim:

1. The method of attaching an implantable tubular graft to the wall of a blood vessel, comprising the steps of:
   forming an incision in said blood vessel;
   inserting said tubular graft into said blood vessel through said incision;
   moving said graft along said blood vessel to a desired location relative to said blood vessel;
   moving an inflatable bulb in a deflated condition within said graft so as to be in a desired position with respect to said graft and blood vessel, said bulb releasably carrying a plurality of clips having outwardly-facing ends;
   quickly inflating said bulb so as to drive said clips outwardly to penetrate said graft and blood vessel;
   releasing said clips after said clips have penetrated said graft and blood vessel;
   deflating said bulb;
   withdrawing such deflated bulb from said blood vessel; and
   closing said incision,
   thereby to leave said graft attached to said blood vessel by said clips.

2. The method as set forth in claim 1, and further comprising the additional step of:
   magnetically holding each clip to said bulb when said bulb is in said deflated condition.

3. The method as set forth in claim 1 wherein said bulb has an annular groove when said body is deflated to receive said clips.

4. The method as set forth in claim 1 wherein each of said clips is U-shaped.

* * * * *